US006836685B1

(12) United States Patent
Fitz

(10) Patent No.: US 6,836,685 B1
(45) Date of Patent: *Dec. 28, 2004

(54) NERVE STIMULATION METHOD AND APPARATUS FOR PAIN RELIEF

(76) Inventor: William R. Fitz, 1967 Collingswood Rd., Columbus, OH (US) 43221

( * ) Notice: Subject to any disclaimer, the term of this patent is extended or adjusted under 35 U.S.C. 154(b) by 0 days.

This patent is subject to a terminal disclaimer.

(21) Appl. No.: 10/018,615

(22) PCT Filed: Jan. 10, 2000

(86) PCT No.: PCT/US00/00544

§ 371 (c)(1),
(2), (4) Date: Mar. 11, 2002

(87) PCT Pub. No.: WO00/78389

PCT Pub. Date: Dec. 28, 2000

Related U.S. Application Data

(63) Continuation of application No. 09/336,241, filed on Jun. 18, 1999, now Pat. No. 6,314,325, which is a continuation-in-part of application No. 09/056,216, filed on Apr. 7, 1998, now Pat. No. 6,014,588.

(51) Int. Cl.[7] .................................................. A61N 1/34
(52) U.S. Cl. ....................................................... 607/46
(58) Field of Search ............................. 607/46, 43, 63

(56) References Cited

U.S. PATENT DOCUMENTS 3,738,368 A * 6/1973 Avery et al. ................. 607/117
6,002,964 A * 12/1999 Feler et al. .................... 607/46
6,058,331 A * 5/2000 King ............................. 607/62
6,104,957 A * 8/2000 Alo et al. ...................... 607/46
6,505,075 B1 * 1/2003 Weiner ......................... 607/46

* cited by examiner

Primary Examiner—Carl Layno
(74) Attorney, Agent, or Firm—Gifford, Krass, Groh, Sprinkle, Anderson & Citkowski, PC

(57) ABSTRACT

Methods, and apparatus are disclosed for stimulation the central, peripheral, and autonomic with particular attention being given to the medial branch (210) of the spinal nerve (212) associated with a painful spinal facet joint so as to block pain impulses from reaching the spinal cord. The preferred apparatus includes a neurostimulator (204), and two or more electrodes (206) which carry electrical pulses to the target nerves. The impulses are intense enough to cause stimulation of a given medial branch (210), and its articular branches, but not so large as to spread to the spinal cord itself. In the preferred embodiment the stimulator (204) is physically small and battery operated facilitating implantation underneath the skin. The stimulator (204) includes a controller (not shown), and appropriate electronics operative to generate electrical impulses tailored to an individual's need for appropriate pain relief in terms of pulse frequency, pulse width, and pulse amplitude. In an alternative embodiment, the stimulator (204) further includes electrodes (206), and electrical circuitry operative to monitor myoelectrical activity generated by the surrounding muscles, and modulate the impulses generated by the stimulator to meet the demands of the individual's activity and/or prolong battery life.

34 Claims, 4 Drawing Sheets

NERVE STIMULATION METHOD AND APPARATUS FOR PAIN RELIEF

REFERENCE TO RELATED APPLICATIONS

This application is a U.S. National Phase of PCT/US00/00544, filed Jan. 10, 2000, which is a continuation of U.S. patent application Ser. No. 09/336,241, filed Jun. 18, 1999, now U.S. Pat. No. 6,314,325, which is a continuation-in-part of U.S. patent application Ser. No. 09/056,216, filed Apr. 7, 1998, now U.S. Pat. No. 6,014,588, the entire contents of all of which are incorporated herein by reference.

FIELD OF THE INVENTION

This invention relates generally to electrically mediated pain relief and, in particular, to the use of electrical current to block sensory pathways. Particular emphasis is given to the medial branch of the spinal nerve root and its articular branches so as to relieve pain caused by painful zygopophysial joints, but the invention can be applied to any portion of the nervous system, including central, autonomic, or peripheral.

BACKGROUND OF THE INVENTION

Pain impulses are transmitted through the peripheral nervous system. Although electrical stimulators have been used to control pain through depolarization of the nerve, this type of treatment is limited by the uncomfortable and often painful effects of the depolarizing electrical stimuli. Indeed, pain from such treatment limits the amount of electrical current that can be applied to the nerve and consequently also limits the amount of pain relief that can be achieved.

The vascular system is modulated by the autonomic nervous system. It has been shown that stimulation of this system at the level of the spinal cord with depolarizing current can improve anginal cardiac pain, vasospasm and arterial insufficiency. However, this type of depolarizing treatment (spinal cord stimulation) is also limited by the uncomfortable nature of the depolarizing current when applied in close proximity to the spinal cord.

A large body of evidence now exists to support the fact that the zygopophysial joints (facet joints) can be pain-producing structures. In particular, it has been shown that the facet joints can be a source of chronic spinal pain in the cervical, thoracic and lumbosacral regions. This pain, which can be due to trauma to and/or degeneration of the facet joint, can be disabling in some patients.

Anatomical dissections reveal that the facet joint is innervated by the articular branches of the medial branch of the spinal nerve. Lesioning this nerve has been shown to relieve pain, but regrowth of the nerve is inevitable and pain returns.

Electrical stimulators of other neural structures has been proposed to provide pain relief. U.S. Pat. No. 5,041,974 to Walker et al, entitled MULTICHANNEL STIMULATOR FOR TUNED STIMULATION, includes a user interface enabling the selection of a channel and the creation of a stimulus wave signal. A slave circuit associated with the channel receives the wave building signal and generates a corresponding low-power stimulus. An output circuit coupled to the slave circuit electronically isolates the stimulus from the other channels, amplifying and converting it to produce a high-fidelity stimulus wave signal.

There have also been developed neuro-type stimulators which are responsive to patient conditions, and adjust their function in accordance therewith. For example, in U.S. Pat. No. 5,031,618 to Mullett, entitled POSITION-RESPONSIVE NEURO STIMULATOR, a position sensor such as a mercury switch which may be used to determine whether a patient is erect or supine, is implanted in the patient. This position information is then used to vary stimulation intensity, in terms of pulse amplitude, pulse width, and a number of pulses per second and other factors. The output of the pulse generator is applied to the spinal cord, peripheral nerves and/or targets in the brain with leads in electrodes in a manner consistent with a given medical need.

To Applicant's knowledge, however, no such neuro stimulators, whether adaptive or fixed in their operation, have been used to hyperpolarize any part of the central, autonomic, or peripheral nervous system. Nor have such techniques been applied to the specific problem of pain relief relative to the zygopophysial or facet joints through depolarization or hyperpolarization of the medial branch nerves. Neuro- stimulators have yet to be used for anodal blockade of the nervous system or, more specifically, stimulation of the medial branches innervating the zygopophysial or facet joints. As the '618 patent points out, stimulation of this type has so far been limited to the treatment of chronic intractable pain requiring spinal cord depolarization.

Accordingly, one object of this invention is to use anodal blockade of electrical nerve impulses in the central, autonomical, and peripheral nervous system.

A further object is to block painful impulses transmitted by the medial branch of the spinal nerve.

Another important object of this invention is to provide apparatus in the form of an electrical nerve stimulator that is implantable, as well as the accompanying electrodes, and methods of using the same.

It is a goal of this invention to create a pain-relief mechanism and accompanying methodology that is long lasting while being minimally invasive so as to reduce medical complications and provide improved pain relief as compared to temporary modalities.

SUMMARY OF THE INVENTION

One aspect of the present invention resides in a method of creating an anodal blockade of the central, autonomic, or peripheral nervous system, with particular emphasis being directed to hyperpolarizing a peripheral nerve or branch of the autonomic nervous system that is external to the spinal column. Although any peripheral nerve or portion of the autonomic nervous system that is external to the spinal canal may be the target of the anodal blockade, the sciatic nerve is of particular interest due to its location and relationship to the vascular system.

According to a preferred method of the invention, a positive electrode (anode) is placed in close proximity, preferably a few millimeters, relative to a target nerve. A negative electrode is placed in an area of low sensitivity at a point remote from the positive electrode, preferably in the adipose tissue. Both of these electrodes could lie under the skin, and may require surgical placement.

The electrodes are connected to a stimulator that generates an electrical current operative to induce the hyperpolarization of the nerve. The stimulator may be implanted under the skin, or may be located outside the body. The stimulator may further include a controller and appropriate electronics operative to generate electrical impulses tailored to an individual's need for appropriate pain relief or modulation of the vascular system in terms of pulse frequency, pulse width, and pulse amplitude.

Another aspect of the present invention resides in methods and apparatus for stimulating the medial branch of the spinal nerve associated with a painful spinal facet joint, so as to block pain impulses from reaching the spinal cord whether through depolarization or hyperpolarization. Broadly, according to an apparatus aspect, the invention is comprised of a neurostimulator and two or more electrodes placed adjacent to the target nerve or nerves. In the preferred embodiment, the apparatus is capable of generating electrical impulses of sufficient intensity to cause stimulation of a given medial branch and its articular branches. Multiple leads with the same polarity may be placed near multiple pain-generating medial and articular branch nerves, with one or more electrodes of the opposite polarity being placed away from the target site. If the electrode adjacent the nerve is a negative electrode, the stimulation is a negative electrical pulse that depolarizes the nerve. If the electrode adjacent the nerve is a positive electrode, the stimulation is a positive electrical pulse which hyperpolarizes the nerve. In any case, the target nerve does not reach threshold and therefore never conducts an impulse.

Although the apparatus may be disposed externally of the individual, in the preferred embodiment the stimulator is physically small and battery operated, facilitating implantation underneath the skin. Accordingly, the components of the stimulator and electrodes are preferably biocompatible and biostable so as not to cause tissue reactions.

The stimulator includes a controller and appropriate electronics operative to generate electrical impulses tailored to an individual's need for appropriate pain relief in terms of pulse frequency, pulse width, and pulse amplitude. In an alternative embodiment, the stimulator further includes electrodes and electrical circuitry operative to monitor myoelectrical activity generated by the surrounding muscles and modulate the impulses generated by the stimulator to meet the demands of the individual's activity and/or to prolong battery life.

DETAILED DESCRIPTION OF THE DRAWINGS

This invention is directed to methods and relative apparatus operative to depolarize or hyperpolarize certain nerves in accordance with electrode placements according to the invention. A particular application is to stimulate one or more medial branches of spinal nerve roots and/or its articular branches to the zygopophysial joints (facet joints) or, through hyperpolarization, any portion of the central, autonomic or peripheral nervous system that subserves a painful area. The articular branches emanate from the medial branch of the spinal nerve and innervate the zygopophysial joints, which have been shown to be a cause of chronic spinal pain.

Broadly, the stimulator includes an electrical nerve stimulator that could be external though, in the preferred embodiment, would be implanted under the skin. This stimulator is connected to electrodes preferably placed subcutaneously adjacent to the medial branch of the spinal nerve and its articular branches.

The stimulator generates an electrical output that would be set to the individual's needs, for example, in terms of pulse frequency, pulse width, and pulse amplitude. This stimulator would create a continuous electrical stimulus or may also be a demand stimulator that is modulated by the surrounding muscular activity that is activated by the individual. The subcutaneous placement of the stimulator could be similar to the implantation of cardiac pacemakers. The placement of the electrodes could be performed under fluoroscopic guidance and with the use of a needle through which the electrode would be threaded. Fluoroscopic guidance is preferred to adequately target the tip of the electrode to within a few millimeters of the targeted nerve.

Figure 1:
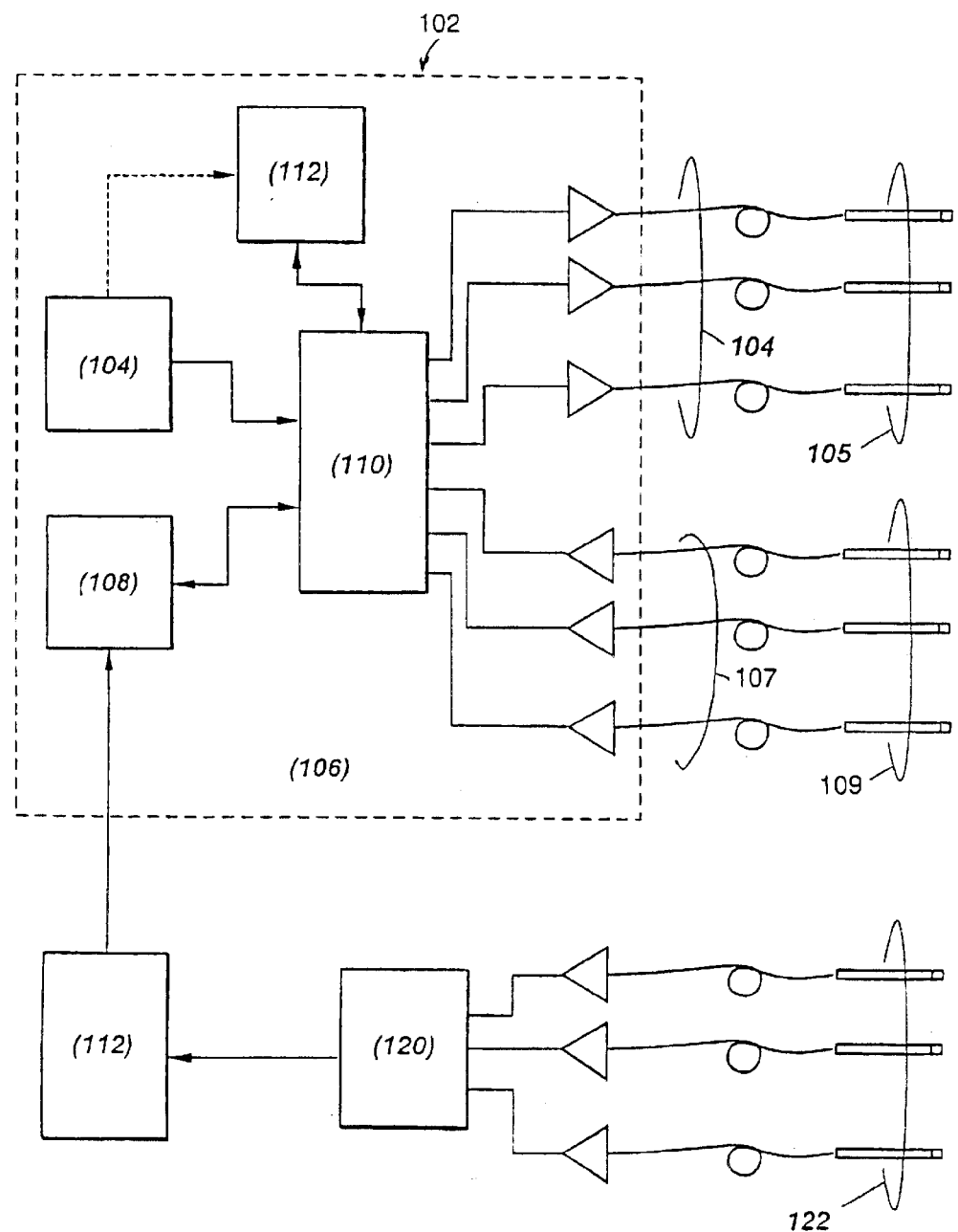
FIG. 1 is a block diagram used to illustrate major electrical subsystems of a stimulator and attachments according to the invention.

As shown in FIG. 1, a preferred apparatus includes a stimulator 102 which generates electrical impulses along lines 103 to a series of positive electrodes 105. The stimulator is also interconnected with a series of negative electrodes 109 by lines 107. In the preferred embodiment, the stimulator 102 is operated by a battery 104 is and encapsulated in a miniaturized package 106 constructed of a biocompatible material, permitting the device to be positioned subcutaneously.

A controller 110, which coordinates overall operation of the device, may be interconnected to a memory 112 for storing output parameters such as pulse frequency, pulse width, or pulse amplitude for a particular patient. Although the memory 112 may be backed-up with battery 104, in the preferred embodiment a non-volatile technology such as an electrically erasable programmable read-only memory (EEPROM) is used to retain the parametric data in the event that the battery needs to be changed. The controller 110 may be of conventional design, such as the 80 C series or equivalent, which is available from the Intel Corp. of Santa Clara, Calif.

The preferred apparatus further includes an interface 108 interconnected to the controller 110, which enables the device to be coupled to programming apparatus 112 prior to implantation. Preferably, the programming apparatus 112 is in the form of a personal computer equipped with an appropriate interface and software enabling the nerve stimulation impulses to be viewed on the screen accompanying the computer and preset for a particular patient in terms of pulse frequency, pulse width, and pulse amplitude. This adjustment prior to implantation may be based upon feedback from the patient, for example, in terms of affected area and/or pain level. Alternatively, an optional input device 120 may be used in conjunction with electrodes 122.

The electrodes 122 may be temporarily implanted and used to sense myoelectrical activity of the surrounding muscles and, based upon the sensed information, adjustments may be made with respect to the output signals. As an alternative, the stimulator itself would incorporate inputs to sense the myoelectrical activity of the surrounding muscles, and this information would be used to modulate the electrical output on an on-demand basis. In either case, the sensing electrode would preferably be implanted in a muscle of the neck or back to detect the myoelectric activity.

The electrodes are preferably composed of a material that conducts electricity, while being covered with a material throughout its length to prevent the spread of the current from the entire length of the electrode. In a preferred embodiment, each electrode comprises a platinum wire coated with Teflon, wherein the distal 2 mm of the tip is denuded of Teflon, thereby creating a site for stimulation at the tip of the electrode. The electrodes are preferably provided in positive/negative pairs, with the positive leads 105 being preferably placed at a distance of two centimeters or more from a corresponding negative lead 109. Depending upon the configuration, a single negative lead may be used in conjunction with a plurality of positive leads, or vice versa.

According to one aspect of the invention, the positive electrodes 105 are implanted subcutaneously with their tips closely adjacent the nerve to be stimulated. The negative electrodes 109 are preferably placed one or more centimeters from the positive electrodes 105. Positive electrical pulses are then provided at the positive electrodes 105 which causes hyperpolarization of the nearby nerve, resulting in an anodal blockade. As mentioned previously, a single negative electrode may be used in place of the multiple electrodes. This approach to anodal blockade of nerve for pain relief purposes may be used for all areas of the nervous system including the brain, spinal cord, and all peripheral nerves. At present, there are no known methods used to block a peripheral nerve, or portion of the autonomic nervous system, which is external to the spinal column through anodal blockade of the nerve.

The approach is especially beneficial for anodal blockade of the medial branches innerviating the zygopophysial or facet joints. For this purpose, a positive electrode 105 is placed adjacent the medial branch of the spinal nerve with the corresponding negative electrode or electrodes spaced therefrom. As an alterative approach, negative electrodes 109 may be implanted subcutaneously near the medial branch of the spinal nerve with the positive electrodes spaced therefrom. Then, negative electrical pulses are applied to the negative electrodes causing depolarization of the nerve and thereby preventing pain impulses traveling along the nerve.

Figure 2:
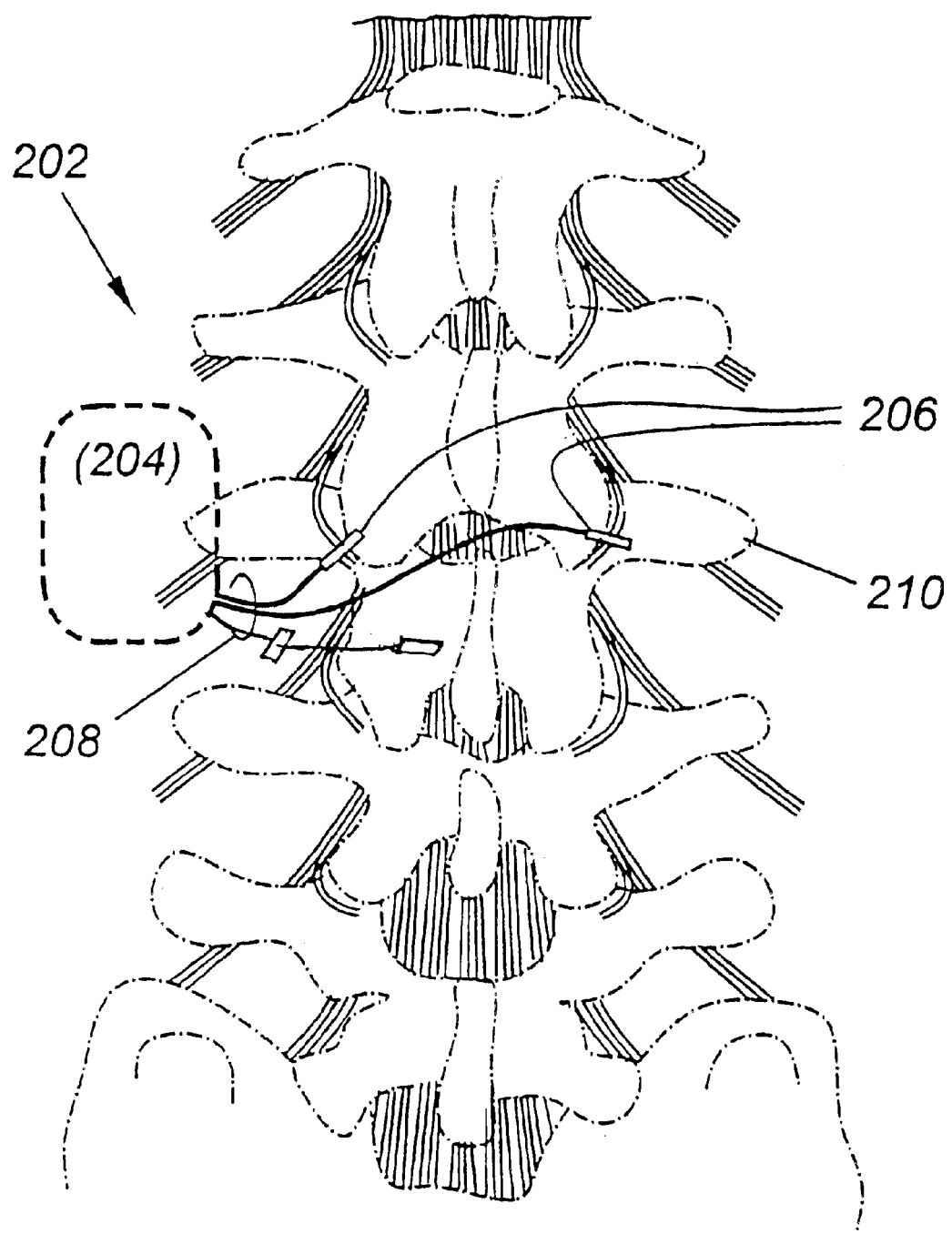
FIG. 2 is a drawing which shows the lower lumbar region of a patient destined to receive placement of the inventive medial branch stimulator and electrode.
Figure 3:
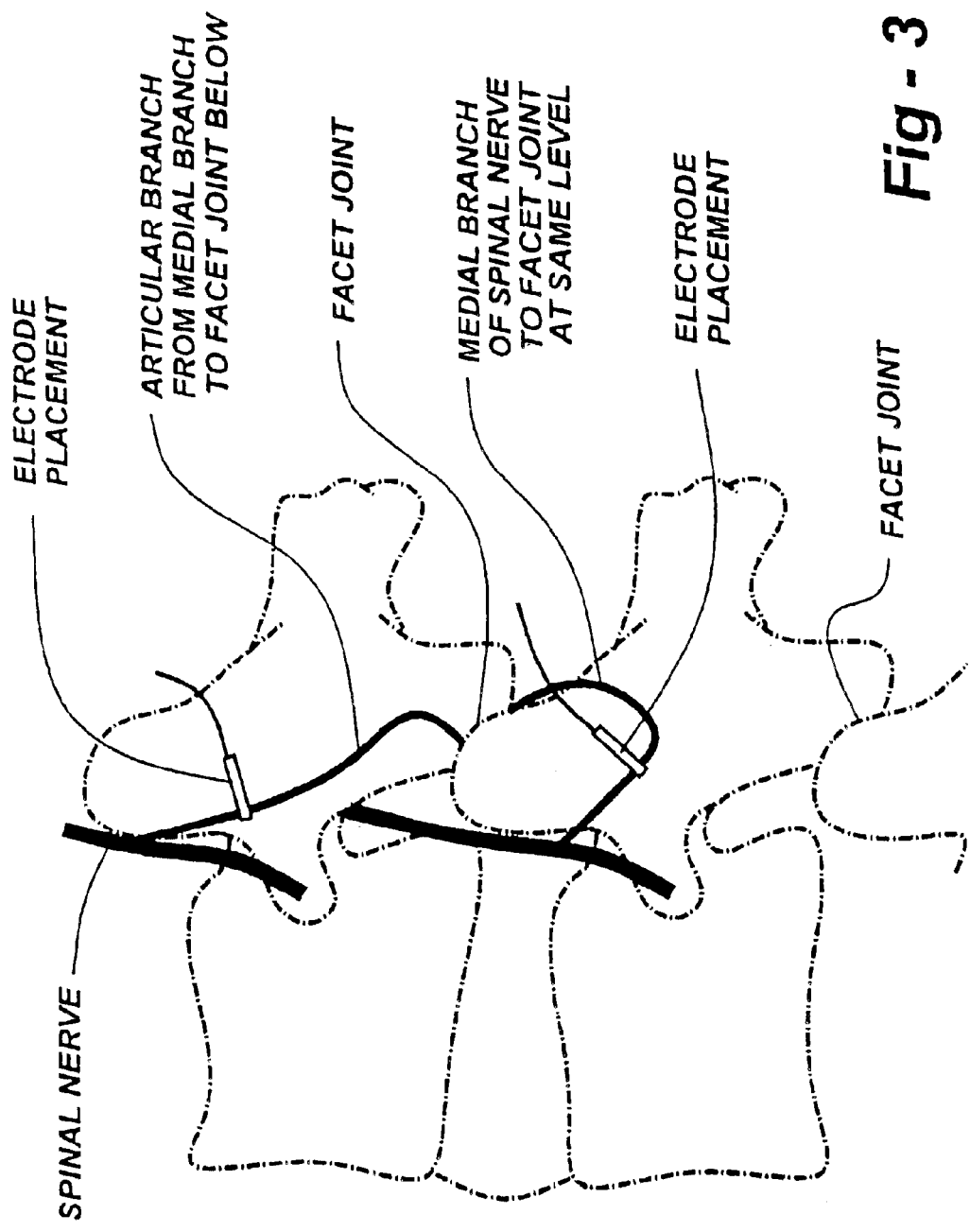
FIG. 3 is a diagram of the medial branch of the spinal nerve showing a preferred electrode placement.

FIG. 2 is a drawing which shows generally at 202 the lower lumbar region of a patient destined to receive the inventive medial branch stimulator 204 and electrode placement. The distal tips 206 of the various leads are then placed near the medial branch 210 of the spinal nerve 212. In the event that multiple medial branch nerves require stimulation, additional leads are provided, as necessary. FIG. 3 illustrates a preferred electrode placement as seen from a side-view perspective.

The invention has also application in modulating pain impulses and/or the vascular system. The blockade is preferably affected by placing the positive pole of an electrode (the anode) in direct proximity to the target nerve, causing the nerve to become hyperpolarized, thereby preventing undesired conduction of impulses. This type of stimulation does not induce pain, and therefore the range of electrical current that can be applied to the nerve for modulation can be expanded for improved pain control or modulation of the vascular system.

The stimulator may be implanted under the skin, or may be external to the skin and connected to electrodes placed under the skin. In a fully implantable embodiment, the stimulator is constructed of any known or yet to be developed biocompatible material. Alternatively, the electrodes may be located superficial to the skin but in close proximity (i.e., within a few millimeters) to a targeted peripheral nerve. The positive electrode (anode) would be placed in close proximity to the nerve and the negative electrode would be placed in a region with low sensitivity to the patient, preferably in the adipose tissue deep to the skin.

Figure 4:
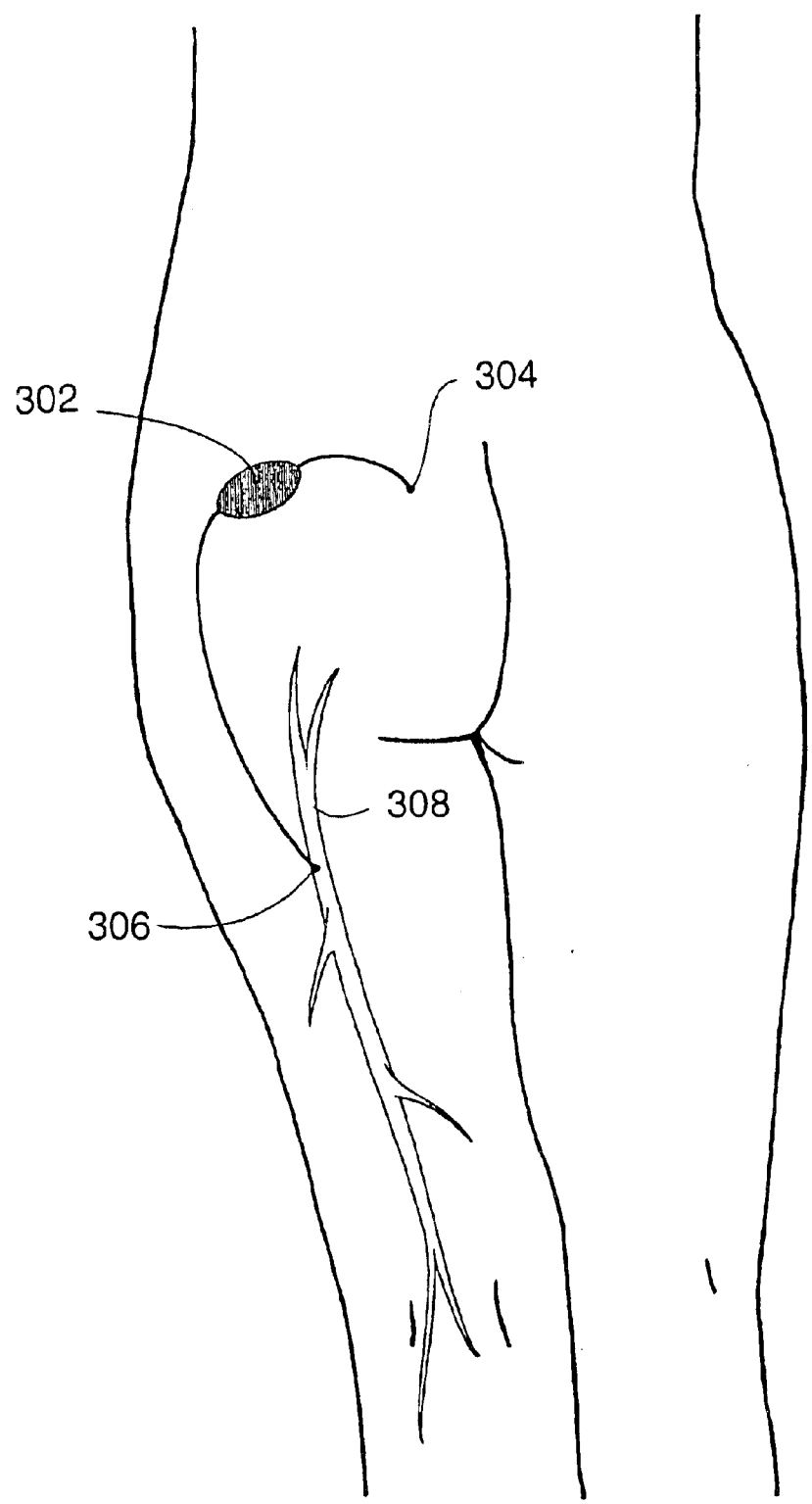
FIG. 4 is a diagram of a stimulator inserted under the skin over the buttock of a patient, with the positive electrode (anode) being placed over the sciatic nerve and the negative electrode being placed in the adipose tissue of the buttock.

FIG. 4 illustrates a stimulator 302 under the skin of a patient, over the buttocks. A positive electrode (anode) 306 is placed over the sciatic nerve 308 and the negative electrode 304 is placed in the adipose tissue of the buttocks. The stimulator generates an electrical output sufficient to cause hyperpolarization of the targeted nerve. A Medtronic Synergy Model 7427 may be used for this purpose. The stimulator may also be adjustable with respect to the needs of the individual in terms of pulse frequency, pulse amplitude, and pulse width.

I claim:

1. Apparatus for relieving zygopophysial joint related pain, comprising:

a stimulator coupled to a plurality of electrodes, each electrode being adapted for placement immediately adjacent to a medial branch of a spinal nerve root, the stimulator including:

a controller operative to generate a series of pulses of sufficient electrical intensity to cause stimulation of a given medial branch and its articular branches, but not so strong as to depolarize or hyperpolarize the spinal cord itself, and operator interface enabling the series of pulses to be tailored as a function of requisite pain relief.

2. The apparatus of claim 1, wherein the stimulator is sealed within an enclosure suitable for implantation.

3. The apparatus of claim 1, wherein the controller is coupled to a second set of electrodes to sense myoelectrical activity generated by the muscles surrounding the medial branch, and wherein the controller is programmed modulate the impulses generated by the stimulator in accordance with the demands of the individual.

4. The apparatus of claim 1, wherein the plurality of electrodes includes at least one positive electrode and more than one negative electrode, the negative electrodes each adapted for placement immediately adjacent to the medial branch of a spinal nerve root, the stimulation of the given medial branch and its articular branches being depolarization of the given medial branch and its articular branches.

5. The apparatus of claim 1, wherein the plurality of electrodes includes at least one negative electrode and more than one positive electrode, the positive electrodes each adapted for placement immediately adjacent to the medial branch of a spinal nerve root, the stimulation of the given medial branch and its articular branches being hyperpolarization of the given medial branch and its articular branches.

6. The apparatus of claim 1, wherein the series of pulses is a series of negative electrical pulses.

7. The apparatus of claim 1, wherein the series of pulses is a series of positive electrical pulses.

8. A method of relieving zygopophysial joint related pain, comprising the steps providing a stimulator coupled to a plurality of electrodes;

placing each electrode immediately adjacent to a medial branch of a spinal nerve root; and generating a series of pulses sufficient to stimulate the medial branch and its articular branches, but not so intense as to spread to the spinal cord itself.

9. The method of claim 8, further including the step of tailoring the pulses to suit the demands of a user of the stimulator.

10. The method of claim 8, further including the steps of:

sensing the myoelectrical activity generated by the muscles surrounding the medial branch, and tailoring the pulses in accordance with the myoelectrical activity.

11. The method of claim 8, further including the step of implanting the stimulator and electrodes beneath the skin.

12. The method of claim 8, further including the step of placing the electrodes under the skin.

13. Apparatus for relieving pain, comprising:
- a stimulator coupled to a plurality of electrodes, each electrode being adapted for placement relative to a nerve,
- the stimulator including:
  - a controller operative to generate a series of positive electrical pulses of sufficient electrical intensity to cause hyperpolarization of the nerve, but not so strong as to spread to the spinal cord itself, and
  - an operator interface enabling the series of pulses to be tailored as a function of requisite pain relief.

14. A method of ameliorating pain and treating vascular disorders, comprising the steps of:
- providing a neural stimulator having one negative electrode and one or more positive electrodes;
- placing at least one of the positive electrodes in close proximity to a peripheral nerve or portion of the autonomic nervous system external to the spinal column of a patient being treated;
- placing the negative electrode remotely from the positive electrode in a region of low sensitivity; and
- providing sufficient energy through the stimulator to hyperpolarize the peripheral nerve or portion of the autonomic nervous system.

15. The method of claim 14, including the step of placing at least one of the positive electrodes proximate to the sciatic nerve.

16. The method of claim 14, including the step of placing the negative electrode in the adipose tissue.

17. The method of claim 14, including the step of placing at least one of the positive electrodes under the skin immediately adjacent the peripheral nerve or portion of the autonomic nervous system.

18. The method of claim 14, including the step of placing the negative electrode under the skin.

19. The method of claim 14, including the step of placing the stimulator under the skin.

20. The method of claim 19, wherein the stimulator is placed in the superior buttock region of the patient.

21. The method of claim 14, further including the step of adjusting a characteristic of energy provided by the stimulator as a function of the needs of the patient.

22. The method of claim 21, wherein the adjusted characteristic is the pulse frequency of the stimulator.

23. The method of claim 21, wherein the adjusted characteristic is the pulse width of the stimulator.

24. The method of claim 21, wherein the adjusted characteristic is the pulse amplitude of the stimulator.

25. A method of ameliorating pain and treating vascular disorders, comprising the steps of:
- providing a neural stimulator having one negative electrode and one or more positive electrodes;
- placing at least one of the positive electrodes under the skin of a patient immediately adjacent the sciatic nerve;
- placing the negative electrode under the skin of the patient in the adipose tissue at a site remote from the positive electrode; and
- providing sufficient energy through the stimulator to hyperpolarize the sciatic nerve.

26. The method of claim 25, including the step of placing the stimulator under the skin in the superior buttock region of the patient.

27. The method of claim 25, further including the step of adjusting the pulse frequency, pulse width, or the pulse amplitude of the stimulator as a function of patient need.

28. A method of ameliorating pain and treating vascular disorders, comprising the steps of:
- providing a neural stimulator having one negative electrode and one or more positive electrodes;
- placing at least one of the positive electrodes in close proximity to a portion of the central nervous system of a patient being treated;
- placing the negative electrode remotely from the positive electrode in a region of low sensitivity; and
- providing sufficient energy through the stimulator to hyperpolarize at least a portion of the central nervous system.

29. The method of claim 28, including the step of placing the negative electrode in the adipose tissue.

30. The method of claim 28, including the step of placing the negative electrode under the skin.

31. The method of claim 28, including the step of placing the stimulator under the skin.

32. The method of claim 28, further including the step of adjusting a characteristic of energy provided by the stimulator as a function of the needs of the patient.

33. The method of claim 32, wherein the adjusted characteristic is the pulse a frequency of the stimulator.

34. The method of claim 32, wherein the adjusted characteristic is the pulse width of the stimulator.

\* \* \* \* \*

UNITED STATES PATENT AND TRADEMARK OFFICE
CERTIFICATE OF CORRECTION

PATENT NO. : 6,836,685 B1
DATED : December 28, 2004
INVENTOR(S) : William R. Fitz It is certified that error appears in the above-identified patent and that said Letters Patent is hereby corrected as shown below:

Title page,
Item [56], References Cited, U.S. PATENT DOCUMENTS, insert the following:
-- 4,570,640     Barsa
   5,504,703     Holsheimer et al.
   5,417,719     Hull et al. --.
Item [57], ABSTRACT,
Line 1, delete "stimulation", insert -- stimulating --.

Signed and Sealed this

Thirtieth Day of August, 2005

JON W. DUDAS
*Director of the United States Patent and Trademark Office*